(12) United States Patent
Winslow et al.

(10) Patent No.: US 7,271,145 B2
(45) Date of Patent: *Sep. 18, 2007

(54) METHODS AND COMPOSITIONS FOR OXYGEN TRANSPORT COMPRISING MODIFIED HEMOGLOBIN IN PLASMA

(75) Inventors: Robert M. Winslow, La Jolla, CA (US); Kim D. Vandegriff, San Diego, CA (US)

(73) Assignee: Sangart, Inc., San Diego, CA (US)

( * ) Notice: Subject to any disclaimer, the term of this patent is extended or adjusted under 35 U.S.C. 154(b) by 299 days.

This patent is subject to a terminal disclaimer.

(21) Appl. No.: 10/501,171

(22) PCT Filed: Jan. 10, 2003

(86) PCT No.: PCT/US03/00695

§ 371 (c)(1),
(2), (4) Date: Sep. 27, 2004

(87) PCT Pub. No.: WO03/059286

PCT Pub. Date: Jul. 24, 2003

(65) Prior Publication Data

US 2005/0020485 A1   Jan. 27, 2005

Related U.S. Application Data

(60) Provisional application No. 60/347,739, filed on Jan. 11, 2002.

(51) Int. Cl.
*A01N 37/18* (2006.01)

(52) U.S. Cl. .......................... 514/2; 514/12; 435/40.5; 435/69.6; 530/300

(58) Field of Classification Search ............... None
See application file for complete search history.

(56) References Cited

U.S. PATENT DOCUMENTS

| | | | |
|---|---|---|---|
| 3,925,344 A | 12/1975 | Mazur | |
| 4,001,401 A | 1/1977 | Bonsen et al. | |
| 4,061,736 A | 12/1977 | Morris et al. | |
| 4,473,496 A | 9/1984 | Scannon | |
| 4,529,719 A | 7/1985 | Tye | |
| 4,584,130 A | 4/1986 | Bocci et al. | |
| 4,600,531 A | 7/1986 | Walder | |
| 4,826,811 A | 5/1989 | Sehgal et al. | |
| 4,857,636 A | 8/1989 | Hsia | |
| 5,028,588 A | 7/1991 | Hoffman et al. | |
| 5,194,590 A | 3/1993 | Sehgal et al. | |
| 5,250,665 A | 10/1993 | Kluger et al. | |
| 5,296,465 A | 3/1994 | Rausch et al. | |
| 5,661,124 A | 8/1997 | Hoffman et al. | |
| 5,814,601 A | 9/1998 | Winslow et al. | |
| 6,054,427 A | 4/2000 | Winslow | |

OTHER PUBLICATIONS

Blumenstein et al. (1978). "Blood Substitutes and Plasma Expanders". Alan R. Liss, editors, New York, New York, pp. 205-212.
Guyton, A.C. (1982). "Human Physiology And Mechanisms Of Disease" 3rd ed., W.B. Saunders Co., Philadelphia, PA, pp. 228-229.
Liebhaber et al. (1980). *P.N.A.S.* 77(12):7054-7058.
Marotta et al. (1977). *J. Biol. Chem.* 252(14):5040-5053.
Nagai et al. (1985). *P.N.A.S.* 82:7252-7255.
Prough, D. et al. (1986). *J. Neurosurg,* 64:627-32.
Przybelski, R.J. et al.(1997). "The pressor effect of hemoglobin—good or bad?" *In Advances in Blood Substitutes.* Winslow, R.M., K.D. Vandegriff, and M. Intaglietta eds., Boston, Birkhauser, pp. 71-85.
Vandergriff and Shrager (1994). "Methods in Enzymology" Everse et al., eds., Academic Press, pp. 232:460.
Winslow et al. (1997). "Advances in Blood Substitutes" Birkhauser ed., Boston MA, pp. 166-188.
Winslow et al. (1977). *J. Biol. Chem.* 252(7):2331-37.

*Primary Examiner*—Hope Robinson
(74) *Attorney, Agent, or Firm*—Gordon & Rees LLP

(57) ABSTRACT

The present invention relates to blood products, and more particularly to compositions comprising a modified hemoglobin in plasma.

5 Claims, No Drawings

METHODS AND COMPOSITIONS FOR OXYGEN TRANSPORT COMPRISING MODIFIED HEMOGLOBIN IN PLASMA

CROSS REFERENCES TO RELATED APPLICATIONS

This application is a 371 of PCT/US03/00695 filed Jan. 10, 2003, which claims the priority of the provisional application No. 60/347,739 filed on Jan. 11, 2002.

TECHNICAL FIELD

The present invention relates to blood substitutes, and more particularly to compositions comprising a modified hemoglobin in plasma.

BACKGROUND OF THE INVENTION

The Circulatory System and the Nature of Hemoglobin

The blood is the means for delivering nutrients to the tissues and removing waste products from the tissues for excretion. The blood is composed of plasma in which red blood cells (RBCs or erythrocytes), white blood cells (WBCs), and platelets are suspended. Red blood cells comprise approximately 99% of the cells in blood, and their principal function is the transport of oxygen to the tissues and the removal of carbon dioxide therefrom.

The left ventricle of the heart pumps the blood through the arteries and the smaller arterioles of the circulatory system. The blood then enters the capillaries, where the majority of the exchange of nutrients and cellular waste products occurs. (See, e.g., A. C. Guyton, Human Physiology And Mechanisms Of Disease (3rd. ed.; W. B. Saunders Co., Philadelphia, Pa.), pp. 228-229 (1982)). Thereafter, the blood travels through the venules and veins in its return to the right atrium of the heart. Though the blood that returns to the heart is oxygen-poor compared to that which is pumped from the heart, when at rest, the returning blood still contains about 75% of the original oxygen content.

The reversible oxygenation function (i.e., the delivery of oxygen) of RBCs is carried out by the protein hemoglobin. In mammals, hemoglobin has a molecular weight of approximately 64,000 daltons and is composed of about 6% heme and 94% globin. In its native form, it contains two pairs of subunits (i.e., it is a tetramer), each containing a heme group and a globin polypeptide chain. In aqueous solution, hemoglobin is present in equilibrium between the tetrameric (MW 64,000) and dimeric forms (MW 32,000); outside of the RBC, the dimers are prematurely excreted by the kidney (plasma half-life of approximately 2-4 hours). Along with hemoglobin, RBCs contain stroma (the RBC membrane), which comprises proteins, cholesterol, and phospholipids.

Exogenous Blood Products

Due to the demand for blood products in hospitals and other settings, extensive research has been directed at the development of blood substitutes and plasma expanders. A blood substitute is a blood product that is capable of carrying and supplying oxygen to the tissues. Blood substitutes have a number of uses, including replacing blood lost during surgical procedures and following acute hemorrhage, and for resuscitation procedures following traumatic injury. Plasma expanders are blood substitutes that are administered into the vascular system but are typically not capable of carrying oxygen. Plasma expanders can be used, for example, for replacing plasma lost from burns, to treat volume deficiency shock, and to effect hemodilution (e.g., for the maintenance of normovolemia and to lower blood viscosity). Essentially, blood substitutes can be used for these purposes or any purpose in which banked blood is currently administered to patients. (See, e.g., U.S. Pat. No. 4,001,401 to Bonson et al., and U.S. Pat. No. 4,061,736 to Morris et al.)

The current human blood supply is associated with several limitations that can be alleviated through the use of an exogenous blood substitute. To illustrate, the widespread availability of safe and effective blood substitutes would reduce the need for banked (allogeneic) blood. Moreover, such blood substitutes would allow the immediate infusion of a resuscitation solution following traumatic injury without regard to cross-matching (as is required for blood), thereby saving valuable time in resupplying oxygen to ischemic tissue. Likewise, blood substitutes can be administered to patients prior to surgery, allowing removal of autologous blood from the patients which could be returned later in the procedure, if needed, or after surgery. Thus, the use of exogenous blood products not only protects patients from exposure to non-autologous (allogeneic) blood, it conserves either autologous or allogeneic (banked, cross-matched) blood for its optimal use.

Limitations of Current Blood Substitutes

Attempts to produce blood substitutes (sometimes referred to as "oxygen-carrying plasma expanders") have thus far produced products with marginal efficacy or whose manufacture is tedious and expensive, or both. Frequently, the cost of manufacturing such products is so high that it effectively precludes the widespread use of the products, particularly in those markets where the greatest need exists (e.g., emerging third-world economies).

Blood substitutes can be grouped into the following three categories: i) perfluorocarbon-based emulsions, ii) liposome-encapsulated hemoglobin, and iii) modified cell-free hemoglobin. As discussed below, none has been entirely successful, though products comprising modified cell-free hemoglobin are thought to be the most promising. Perfluorochemical-based compositions dissolve oxygen as opposed to binding it as a chelate. In order to be used in biological systems, the perfluorochemical must be emulsified with a lipid, typically egg-yolk phospholipid. Though the perfluorocarbon emulsions are inexpensive to manufacture, they do not carry sufficient oxygen at clinically tolerated doses to be effective. Conversely, while liposome-encapsulated hemoglobin has been shown to be effective, it is far too costly for widespread use. (See generally, Winslow, Robert M., "Hemoglobin-based Red Cell Substitutes", Johns Hopkins University Press, Baltimore, 1992).

Most of the blood substitute products in clinical trials today are based on modified hemoglobin. These products, frequently referred to as hemoglobin-based oxygen carriers (HBOCs), generally comprise a homogeneous aqueous solution of a chemically-modified hemoglobin, essentially free from other red cell residue (stroma). Although stroma-free hemoglobin (SFH) from humans is the most common raw material for preparing a HBOC, other sources of hemoglobin have also been used. For example, hemoglobin can be obtained or derived from animal blood (e.g., bovine or porcine hemoglobin) or from bacteria or yeast or transgenic animals molecularly altered to produce a desired hemoglobin product.

The chemical modification is generally one of intramolecular cross-linking, oligomerization and/or polymer conjugation to modify the hemoglobin such that its persistence in the circulation is prolonged relative to that of unmodified hemoglobin, and its oxygen binding properties are similar to those of blood. Intramolecular cross-linking chemically binds together subunits of the tetrameric hemoglobin unit to prevent the formation of dimers which, as previously indicated, are prematurely excreted. (See, e.g., U.S. Pat. No. 5,296,465 to Rausch et al.)

The high costs of manufacturing HBOC products have greatly limited their commercial viability. In addition, the present inventors have found that known HBOCs have a tendency to release excessive amounts of oxygen to the tissues at the arteriole walls rather than the capillaries. This can result in insufficient oxygen available for delivery by the HBOC to the tissues surrounding the capillaries. This is despite the fact that the initial loading of the HBOC with oxygen may be relatively high, even higher than that normally achieved with natural red blood cells.

In addition, most blood substitutes under development are limited to HBOCs in colloid solutions and solutions having relatively low osmolarity. (See, e.g., U.S. Pat. Nos. 5,814,601 and 5,661,124). While such mixtures are sufficient for some blood replacement uses, an enhancement of the therapeutic effects of the blood substitute is desired for other uses. Such enhancement can be provided by supplying the HBOC in plasma. This provides the dual benefit of enhancing the delivery of oxygen to the tissues and providing the benefit of plasma replacement. Accordingly, the present invention relates to a blood substitute that comprises HBOC in plasma.

SUMMARY OF THE INVENTION

The present invention relates to the use of surface-modified hemoglobins in plasma as blood substitutes. The plasma may be from a natural source, and is preferably from the same animal species as the hemoglobin. More preferably, the plasma is autologous plasma, i.e., it comes from the recipient themselves. Other aspects of the present invention are described throughout the specification.

DESCRIPTION OF THE INVENTION

The present invention is directed to blood substitutes comprising HBOCs and plasma. For certain applications, there is a synergistic effect of enhancing oxygen delivery using HBOCs and administering plasma.

Definitions

To facilitate understanding of the invention set forth in the disclosure that follows, a number of terms are defined below.

The term "hemoglobin" refers generally to the protein contained within red blood cells that transports oxygen. Each molecule of hemoglobin has 4 subunits, 2 $\alpha$ chains and 2 $\beta$ chains, which are arranged in a tetrameric structure. Each subunit also contains one heme group, which is the iron-containing center that binds oxygen. Thus, each hemoglobin molecule can bind 4 oxygen molecules.

The term "modified hemoglobin" includes, but is not limited to, hemoglobin altered by a chemical reaction such as intra- and inter-molecular cross-linking, genetic manipulation, polymerization, and/or conjugation to other chemical groups (e.g., polyalkylene oxides, for example polyethylene glycol, or other adducts such as proteins, peptides, carbohydrates, synthetic polymers and the like). In essence, hemoglobin is "modified" if any of its structural or functional properties have been altered from its native state. As used herein, the term "hemoglobin" by itself refers both to native, unmodified, hemoglobins as well as modified hemoglobin.

The term "surface-modified hemoglobin" is used to refer to hemoglobin described above to which chemical groups such as dextran or polyalkylene oxide have been attached, most usually covalently.

The term "stroma-free hemoglobin" refers to hemoglobin from which all red blood cell membranes have been removed.

The term "perfluorocarbons" refers to synthetic, inert, molecules that contain fluorine atoms, and that consist entirely of halogen (Br, F, Cl) and carbon atoms. In the form of emulsions, they are under development as blood substances, because they have the ability to dissolve many times more oxygen than equivalent amounts of plasma or water.

The term "plasma expander" refers to any solution that may be given to a subject to treat blood loss.

The term "oxygen carrying capacity", or simply "oxygen capacity" refers to the capacity of a blood substitute to carry oxygen, but does not necessarily correlate with the efficiency in which it delivers oxygen. Oxygen carrying capacity is generally calculated from hemoglobin concentration, since it is known that each gram of hemoglobin binds 1.34 ml of oxygen. Thus, the hemoglobin concentration in g/dl multiplied by the factor 1.34 yields the oxygen capacity in ml/dl. Hemoglobin concentration can be measured by any known method, such as by using the B-Hemoglobin Photometer (HemoCue, Inc., Angelholm, Sweden). Similarly, oxygen capacity can be measured by the amount of oxygen released from a sample of hemoglobin or blood by using, for example, a fuel cell instrument (e.g., Lex-$O_2$-Con; Lexington Instruments).

The term "oxygen affinity" refers to the avidity with which an oxygen carrier such as hemoglobin binds molecular oxygen. This characteristic is defined by the oxygen equilibrium curve which relates the degree of saturation of hemoglobin molecules with oxygen (Y axis) with the partial pressure of oxygen (X axis). The position of this curve is denoted by the value, P50, the partial pressure of oxygen at which the oxygen carrier is half-saturated with oxygen, and is inversely related to oxygen affinity. Hence the lower the P50, the higher the oxygen affinity. The oxygen affinity of whole blood (and components of whole blood such as red blood cells and hemoglobin) can be measured by a variety of methods known in the art. (See, e.g., Winslow et al., J. Biol. Chem. 252(7):2331-37 (1977)). Oxygen affinity may also be determined using a commercially available HEMOX™ TM Analyzer (TCS Scientific Corporation, New Hope, Pa.). (See, e.g., Vandegriff and Shrager in Methods in Enzymology (Everse et al., eds.) 232:460 (1994)).

The terms "hypertonic" and "hyperosmolar" means an osmolarity greater than 800 mOsm/l, which is the average osmolarity of whole blood. The phrase "highly hypertonic" refers to solutions with an osmolarity greater than 2000 mOsm/l. Osmolarity may be measured by any suitable technique, such as in a Wescor instrument (Ontario, Canada).

The term "oxygen-carrying component" refers broadly to a substance capable of carrying oxygen in the body's circulatory system and delivering at least a portion of that oxygen to the tissues. In preferred embodiments, the oxygen-carrying component is native or modified hemoglobin, and is also referred to herein as a "hemoglobin based oxygen carrier", or "HBOC".

The term "hemodynamic parameters" refers broadly to measurements indicative of blood pressure, flow and volume status, including measurements such as blood pressure, cardiac output, right atrial pressure, and left ventricular end diastolic pressure.

The term "crystalloid" refers to small molecules (usually less than 10 Å) such as salts, sugars, and buffers. Unlike colloids, crystalloids do not contain any oncotically active components and therefore leave the circulation very quickly.

The term "colloid", in contrast to "crystalloid" refers to larger molecules (usually greater than 10 Å) that do not freely pass through biological membranes and includes proteins such as albumin and gelatin, as well as starches such as pentastarch and hetastarch.

The term "colloid oncotic pressure" or "colloid osmotic pressure" refers to the propensity of colloids to remain in the interavascular space for prolonged periods of time drawing water from the interstitial and intracellular spaces into the intravascular space.

Finally, the term "mixture" refers to a mingling together of two or more substances without the occurrence of a reaction by which they would lose their individual properties; the term "solution" refers to a liquid mixture; the term "aqueous solution" refers to a solution that contains some water and may also contain one or more other liquid substances with water to form a multi-component solution; the term "approximately" refers to the actual value being within a range, e.g. 10%, of the indicated value. The meaning of other terminology used herein should be easily understood by someone of reasonable skill in the art.

The Nature of Oxygen Delivery and Consumption

Although the successful use of the compositions and methods of the present invention do not require comprehension of the underlying mechanisms of oxygen delivery and consumption, basic knowledge regarding some of these putative mechanisms may assist in understanding the discussion that follows. It has generally been assumed that the capillaries are the primary conveyors of oxygen to the tissue. However, regarding tissue at rest, current findings indicate that there is approximately an equipartition between arteriolar and capillary oxygen release. That is, hemoglobin in the arterial system is believed to deliver approximately one third of its oxygen content in the arteriolar network and one-third in the capillaries, while the remainder exits the microcirculation via the venous system.

The arteries themselves are sites of oxygen utilization. For example, the artery wall requires energy to effect regulation of blood flow through contraction against vascular resistance. Thus, the arterial wall is normally a significant site for the diffusion of oxygen out of the blood. However, current oxygen-delivering compositions (e.g., HBOCs) may release too much of their oxygen content in the arterial system, and thereby induce an autoregulatory reduction in capillary perfusion. Accordingly, the efficiency of oxygen delivery of a blood substitute may actually be hampered by having too much oxygen or too low an oxygen affinity.

The rate of oxygen consumption by the vascular wall, i.e., the combination of oxygen required for mechanical work and oxygen required for biochemical synthesis, can be determined by measuring the gradient at the vessel wall. See, e.g., Winslow, et al., in "Advances in Blood Substitutes" (1997), Birkhauser, ed., Boston, Mass., pages 167-188. Present technology allows accurate oxygen partial pressure measurements in a variety of vessels. The measured gradient is directly proportional to the rate of oxygen utilization by the tissue in the region of the measurement. Such measurements show that the vessel wall has a baseline oxygen utilization which increases with increases in inflammation and constriction, and is lowered by relaxation.

The vessel wall gradient is inversely proportional to tissue oxygenation. Vasoconstriction increases the oxygen gradient (tissue metabolism), while vasodilation lowers the gradient. Higher gradients are indicative of the fact that more oxygen is used by the vessel wall, while less oxygen is available for the tissue. The same phenomenon is believed to be present throughout the microcirculation.

Oxygen Carrying Component

In preferred embodiments, the oxygen carrier (i.e., the oxygen-carrying component) is a hemoglobin-based oxygen carrier, or HBOC. The hemoglobin may be either native (unmodified); subsequently modified by a chemical reaction such as intra- or inter-molecular cross-linking, polymerization, or the addition of chemical groups (e.g., polyalkylene oxides, or other adducts); or it may be recombinantly engineered. Human alpha- and beta-globin genes have both been cloned and sequenced. Liebhaber, et al., P.N.A.S. 77: 7054-7058 (1980); Marotta, et al., J. Biol. Chem. 353: 5040-5053 (1977) (beta-globin cDNA). In addition, many recombinantly produced modified hemoglobins have now been produced using site-directed mutagenesis, although these "mutant" hemoglobin varieties were reported to have undesirably high oxygen affinities. See, e.g., Nagai, et al., P.N.A.S. 82: 7252-7255 (1985).

The present invention is not limited by the source of the hemoglobin. For example, the hemoglobin may be derived from animals and humans. Preferred sources of hemoglobin are humans, cows and pigs. In addition, hemoglobin may be produced by other methods, including chemical synthesis and recombinant techniques. The hemoglobin can be added to the blood product composition in free form, or it may be encapsulated in a vesicle, such as a synthetic particle, microballoon or liposome. The present invention also contemplates the use of other means for oxygen delivery that do not entail hemoglobin or modified hemoglobin, such as the fluorocarbon emulsions.

The preferred oxygen-carrying components of the present invention should be stroma free and endotoxin free. Representative examples of oxygen-carrying components are disclosed in a number of issued United States Patents, including U.S. Pat. No. 4,857,636 to Hsia; U.S. Pat. No. 4,600,531 to Walder, U.S. Pat. No. 4,061,736 to Morris et al.; U.S. Pat. No. 3,925,344 to Mazur; U.S. Pat. No. 4,529,719 to Tye; U.S. Pat. No. 4,473,496 to Scannon; U.S. Pat. No. 4,584,130 to Bocci et al; U.S. Pat. No. 5,250,665 to Kluger et al.; U.S. Pat. No. 5,028,588 to Hoffman et al.; and U.S. Pat. No. 4,826,811 and U.S. Pat. No. 5,194,590 to Sehgal et al.

However, as discussed above, the present inventors theorize that blood substitutes with lower oxygen affinities may trigger autoregulatory events that prevent oxygen delivery to the tissues via microcapillary circulation. Accordingly, using the experimental models described in Winslow, supra, it has been determined that, for some applications an HBOC with an oxygen affinity less than that of SFH is desired. This finding is contrary to conventional teachings in the field.

There are many different scientific approaches to manufacturing HBOCs with high oxygen affinity (i.e. those with P50s less than SFH). For example, studies have identified the amino acid residues that play a role in oxygen affinity, and thus site-directed mutagenesis can now be easily carried out to manipulate oxygen affinity to a desired level. See, e.g., U.S. Pat. No. 5,661,124. Many other approaches are discussed in U.S. Pat. No. 6,054,427.

Modifications of the Oxygen-Carrying Component

In a preferred embodiment, the oxygen-carrying component is modified hemoglobin. A preferred modification to hemoglobin is "surface-modification", i.e. covalent attachment of chemical groups to the exposed amino acid side chains on the hemoglobin molecule. Most commonly, the chemical group attached to the hemoglobin is polyethylene glycol (PEG), because of its pharmaceutical acceptability and commercial availability. PEGs are polymers of the general chemical formula $H(OCH_2CH_2)_nOH$, where n is greater than or equal to 4. PEG formulations are usually followed by a number that corresponds to their average molecular weight. For example, PEG-200 has an average molecular weight of 200 and may have a molecular weight range of 190-210. PEGs are commercially available in a number of different forms, and in many instances come preactivated and ready to conjugate to proteins.

The number of PEGs to be added to the hemoglobin molecule may vary, depending on the size of the PEG. However, the molecular size of the resultant modified hemoglobin should be sufficiently large to avoid being cleared by the kidneys to achieve the desired half-life. Blumenstein, et al., determined that this size is achieved above 84,000 molecular weight. (Blumenstein, et al., in "Blood Substitutes and Plasma Expanders", Alan R. Liss, editors, New York, N.Y., pages 205-212 (1978).) Therein, the authors conjugated hemoglobin to dextran of varying molecular weight. They reported that a conjugate of hemoglobin (with a molecular weight of 64,000) and dextran (having a molecular weight of 20,000) "was cleared slowly from the circulation and negligibly through the kidneys", but increasing the molecular weight above 84,000 did not alter the clearance curves. Accordingly, as determined by Blumenstein, et al., it is preferable that the HBOC have a molecular weight of at least 84,000.

Plasma Component

The blood substitutes of the present invention further comprise plasma, preferably animal plasma, and more preferably human plasma. Although not wishing to be bound by any particular scientific theory, it is believed that the administration of blood substitutes may dilute the concentration of coagulation factors to an undesirable level. Accordingly, using plasma as the diluent for the oxygen carrying component avoids this problem. Plasma can be collected by any means known in the art, provided that red cells, white cells and platelets are essentially removed. Preferably, it is obtained using an automated plasmaphoresis apparatus. Plasmaphoresis apparatuses are commercially available and include, for example, apparatuses that separate plasma from the blood by ultrafiltration or by centrifugation. An ultrafiltration-based plasmaphoresis apparatus such as manufactured by Auto C, A200 (Baxter International, Largo, Fla.) is suitable because it effectively removes red cells, white cells and platelets while preserving coagulation factors.

Plasma may be collected with an anticoagulant, many of which are well known in the art. Preferred anti-coagulants are those that chelate calcium such as citrate. Sodium Citrate at 0.38% (final concentration in the plasma) is the preferred anticoagulant for collecting plasma. The plasma may be fresh, frozen, pooled and/or sterilized.

In addition to plasma from natural sources, it is contemplated that synthetic plasma is also included within the present invention, and includes any aqueous solution that is at least isotonic and that further comprises at least one plasma protein.

While plasma from exogenous sources may be preferred, it is also within the present invention to use autologous plasma that is collected from the subject prior to formulation and administration of the blood substitute.

Crystalloid Component

In one embodiment of the present invention, the blood substitute may also comprise a crystalloid. The crystalloid component can be any crystalloid which, in the form of the blood substitute composition, is preferably capable of achieving an osmolarity greater than 800 mOsm/l, i.e. it makes the blood substitute "hypertonic". Examples of suitable crystalloids and their concentrations in the blood substitute include, e.g., 3% NaCl, 7% NaCl, 7.5% NaCl, and 7.5% NaCl in 6% dextran. More preferably, the blood substitute has an osmolarity of between 800 and 2400 mOsm/l. The use of recombinantly produced hemoglobins in solutions with an osmolality between 300-800 mOsm/l that further comprise a colloid (i.e. a molecule less diffusible than dextrose) have been previously reported. See, e.g., U.S. Pat. No. 5,661,124. However, this patent teaches away from producing blood substitutes with osmolalities above 800, and suggests that the hemoglobin concentration should be between 6-12 g/dl. In contrast, the oxygen carrying efficiency of compositions of the present invention permit lower concentrations of hemoglobin to be used, such as less than 6 g/dl or even less than 4 g/dl.

When the blood substitute further comprises a crystalloid and is hypertonic, the compositions of present invention may provide improved functionality for rapid recovery of hemodynamic parameters over other blood substitute compositions, which include a colloid component. Small volume highly hypertonic crystalloid infusion (e.g., 1-10 ml/kg) provides significant benefits in the rapid and sustained recovery of acceptable hemodynamic parameters in controlled hemorrhage. (See, e.g., Przybelski, R. J., E. K. Daily, and M. L. Birnbaum, "The pressor effect of hemoglobin—good or bad?" In Winslow, R. M., K. D. Vandegriff, and M. Intaglietta, eds. Advances in Blood Substitutes. Industrial Opportunities and Medical Challenges. Boston, Birkhauser (1997), 71-85). Hypertonic crystalloid solutions alone, however, do not adequately restore cerebral oxygen transport. See D. Prough, et al., Effects of hypertonic saline versus Ringer's solution on cerebral oxygen transport during resuscitation from hemorrhagic shock J. Neurosurg. 64:627-32 (1986).

Formulation

The blood substitutes of the present invention are formulated by mixing the oxygen carrier and other optional excipients with a suitable diluent that is at least 40% plasma. Although the concentration of the oxygen carrier in the diluent may vary according to the application, and in particular based on the expected post-administration dilution, in preferred embodiments, because of the other features of the compositions of the present invention that provide for enhanced oxygen delivery and therapeutic effects, it is usually unnecessary for the concentration to be above 6 g/dl, and is more preferably between 0.1 to 4 g/dl.

Clinical Applications

The methods and compositions of the present invention are useful in a variety of different applications, such as hemodilution, trauma, septic shock, ischemia, cancer, anemia, cardioplegia, hypoxia and organ perfusion. These and other applications are discussed extensively in U.S. Pat. No. 6,054,427.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in hematology, surgical science, transfusion medicine, transplantation, or any related fields are intended to be within the scope of the following claims.

We claim:

1. A blood substitute composition comprising polyethylene glycol surface-modified hemoglobin having an oxygen affinity less than that of stroma-free hemoglobin, and an aqueous diluent, wherein the aqueous diluent is at least 40% plasma.

2. The blood substitute composition of claim 1, wherein the plasma is derived from a natural source.

3. The blood substitute composition of claim 1, wherein the plasma is derived from the same animal species as the hemoglobin.

4. The blood substitute composition of claim 1, wherein the plasma is autologous plasma.

5. The blood substitute composition of claim 1, wherein the hemoglobin concentration is less than 4g/dL.

* * * * *